United States Patent [19]

Moore et al.

[11] Patent Number: 5,773,790
[45] Date of Patent: Jun. 30, 1998

[54] BEAM BLOCKING MATERIAL AND METHOD FOR BEAM DRILLING AND INSPECTING COOLING HOLES

[75] Inventors: James R. Moore; Gary E. Wheat, both of Madisonville, Ky.

[73] Assignee: General Electric Company, Cincinnati, Ohio

[21] Appl. No.: 925,906

[22] Filed: Sep. 9, 1997

Related U.S. Application Data

[63] Continuation of Ser. No. 786,132, Jan. 21, 1997, abandoned.

[51] Int. Cl.[6] .................................................. B23K 26/00
[52] U.S. Cl. ................................. 219/121.71; 219/121.83
[58] Field of Search ........................... 219/121.7, 121.71, 219/121.83, 121.85; 29/889.721; 382/152; 356/237, 428, 432; 250/302, 461.1, 459.1, 484.4

[56] References Cited

U.S. PATENT DOCUMENTS

| | | | |
|---|---|---|---|
| 3,607,333 | 9/1971 | Alburger | 250/302 X |
| 3,624,397 | 11/1971 | Honeycutt et al. | 250/302 |
| 3,806,252 | 4/1974 | Harris et al. | 356/237 X |
| 3,880,790 | 4/1975 | McLaren et al. | 523/139 |
| 3,904,545 | 9/1975 | Molina | 250/302 X |
| 4,377,492 | 3/1983 | Jones | 252/301.19 |
| 4,447,152 | 5/1984 | Rainford et al. | 356/237 |
| 4,644,162 | 2/1987 | Bantel et al. | . |
| 4,873,414 | 10/1989 | Ma et al. | . |
| 5,011,626 | 4/1991 | Ma et al. | . |
| 5,049,722 | 9/1991 | Corfe et al. | . |
| 5,054,087 | 10/1991 | Carbon et al. | . |
| 5,111,046 | 5/1992 | Bantel | . |
| 5,247,766 | 9/1993 | Kildea | . |
| 5,286,947 | 2/1994 | Clyde et al. | . |
| 5,517,310 | 5/1996 | Paquette | 382/152 X |
| 5,614,114 | 3/1997 | Owen | 219/121.66 |

FOREIGN PATENT DOCUMENTS

| | | | |
|---|---|---|---|
| 4-41090 | 2/1992 | Japan | 219/121.7 |
| 4-165057 | 6/1992 | Japan | . |

OTHER PUBLICATIONS

Ready, J. F., Industrial Applications of Lasers, Academic Press, New York, 1978, pp. 336–357.

Hecht, J. The Laser Guidebook 2nd Edition, McGraw–Hill, New York, 1992, p. 488.

Primary Examiner—Gregory L. Mills
Attorney, Agent, or Firm—Andrew C. Hess; Nathan D. Herkamp

[57] ABSTRACT

A method of forming and inspecting beam drilled holes, and in particular laser beam drilled holes, in an article, such as a turbine blade or vane airfoil, with a hollow interior. The method includes (a) filling the hollow interior with a beam blocking material having fluorescent material, (b) beam drilling the holes in the wall through to the hollow interior, and (c) inspecting the hole under an ultraviolet light. The beam blocking material preferably includes a wax material and step (a) includes filling the hollow interior with a melted mixture of the wax and fluorescent materials. The wax material may be a pattern wax material suitable for use in making turbine blade investment casting molds and the fluorescent material may be a fluorescent penetrant.

5 Claims, 4 Drawing Sheets

BEAM BLOCKING MATERIAL AND METHOD FOR BEAM DRILLING AND INSPECTING COOLING HOLES

This application is a Continuation of application Ser. No. 08/786,132, filed Jan. 21, 1997, now abandoned.

BACKGROUND OF THE INVENTION

1. Field of the Invention

The present invention relates to the detection of blocked or defective laser drilled cooling holes and, more particularly, to material and method for beam drilling and inspecting the cooling holes of a gas turbine engine airfoil using an ultraviolet light to illuminate a fluorescent laser beam blocking material used during beam and, more particularly, laser drilling of the holes.

2. Discussion of the Background Art

Gas turbine engines have hollow airfoil turbine blades and vanes representative of hollow articles having laser or otherwise beam drilled cooling holes to which this patent is directed. Referring to FIGS. 1 & 2, a gas turbine engine blade 10 and more particularly its airfoil 11 has a multiplicity of cooling channels or holes 12 formed therein by laser drilling to permit cooling of the blade during engine operation. The cooling holes 12 extend from an exterior surface 14 of a wall 15 of the blade 10 into a hollow interior 16 or plenum of the blade 10. The blade hollow interior includes a plurality of interior walls 18 or baffles to direct cooling air along a serpentine cooling circuit 19 further indicated by arrows 20, through the interior of blade 10 and out cooling holes 12 to create cooling air streams, indicated by arrows 22. Cooling air 20 absorbs heat within the interior 16 of blade 10 and also from the walls surrounding cooling holes 12 and cooling air streams 22 exiting holes 12 flow over the exterior surface 14 to further cool the blade.

In order to function properly, the cooling holes 12 must be constructed to a known configuration because the distribution of airflow must be controlled to achieve proper cooling of the blade during engine operation. Thus, the cooling holes must not be blocked or even partially blocked to provide sufficient and uniform cooling air distribution through blade interior 16 and across the exterior 14 of blade 10. Laser drilling and other beam drilling processes create melted material and the holes may become blocked after the drilling procedure is finished. Sometimes individual holes in an array of holes are not drilled through completely or missed altogether due to an error in the drilling process or faulty equipment. Therefore, the inspection of cooling holes 12 to detect blockages is very important in the process of making such articles, particularly from a quality control standpoint. Inspection of cooling holes 12 to detect blockages is difficult because of the small size of the holes; a typical hole diameter is about 12 mils (0.3 mm.). A wire or pin diameter gage is typically employed to inspect the cooling holes for blockage but this method is time consuming, tedious and labor intensive. Additionally, the wire or pin gauges can break and pieces of the gauge can become trapped within the interior plenum or the cooling hole and, therefore, block the hole adding further time and costs to the manufacturing process.

A method and apparatus for inspecting cooling holes using infrared thermography is disclosed and claimed in U.S. Pat. No. 4,644,162, issued Feb. 17, 1987. This patent discloses forcing a heated gas through a relatively cooler cooling hole, measuring the infrared signature of the cooling holes during the transient with a scanning infrared radiometer, and comparing the measured radiation intensity with a reference. Another method and apparatus for inspecting a channel through a workpiece or cooling holes through the surface of a gas turbine engine are disclosed in U.S. Pat. No. 5,111,046 which uses imaging with an infrared radiometer to generate a series of images of the blade during both heat-up and cool-down cycles. A selected group of parameters are determined from the series of images generated by the IR radiometer and defects within the cooling holes may then be detected by analyzing the parameters, such as a transient response of the infrared signature of the cooling holes during both the heat-up and the cool-down cycles. Again, both these methods though very useful are very expensive and time consuming to incorporate in a production line such as is the intended use of the present invention.

A method and apparatus real-time cooling hole size monitoring and laser control to enhance the quality and consistency of cooling holes is disclosed in U.S. Pat. No. 4,873,414. This method and apparatus monitor light reflected back from the hole to provide a means for monitoring the size of the hole being drilled by the laser and for controlling the laser beam. U.S. Pat. No. 5,011,626 discloses a barrier material that is placed in front of those surfaces in the hollow interior that one wishes to protect from the laser beam. The barrier material includes material which will disperse the laser light and material which will emit light when exposed to the laser light. The light emitter materials could be luminescent materials, phosphorescent materials, or fluorescent materials. These apparatus methods provide means for monitoring the quality of the cooling hole during the laser hole drilling process but will not find remelt blockage which occurs after the laser or another hole drilling beam is turned off.

U.S. Pat. No. 5,054,087 discloses a process for optically checking perforations in a hollow article, particularly the micro-perforations in the vicinity of the leading or trailing edge of a hollow turbine blade for a turbo-shaft engine. This process comprises illuminating the inner cavity (hollow interior) of the article through an opening at one end thereof and scanning the length of the article by means of a video camera. The video signals are then processed and compared to signals with a predetermined train of reference signals derived from a standard article.

Such a system may work for non-serpentine cooling circuits but cannot reach interior cavities of the serpentine type or any other type of hidden cavities and cooling circuits inside of the cooled airfoil. Often there is no way for light to be directed into the interior cavities of leading edge cooling chambers to which the cooling holes are laser drilled.

The present invention is directed to overcoming these shortcomings and provide an accurate, quick, and inexpensive method of inspecting laser drilled cooling holes.

These features and advantages will become more readily apparent in the following description when taken in conjunction with the appended drawings.

SUMMARY OF THE INVENTION

A method of forming and inspecting beam drilled holes and, in particular, laser beam drilled holes, in an article, such as a turbine blade or vane airfoil with a hollow interior. The method includes (a) filling the hollow interior with a beam blocking material having fluorescent material, (b) beam drilling the holes in the wall through to the hollow interior, and (c) inspecting the hole under an ultraviolet light. The beam drilling step (a) preferably includes laser drilling. The beam blocking material preferably includes a wax material and step (a) includes filling the hollow interior with a melted mixture of the wax and fluorescent materials. The wax material may be a pattern wax material suitable for use in making turbine blade investment casting molds and the fluorescent material may be a fluorescent penetrant several of which are commonly known and used in the art to detect cracks.

The present invention also includes the various embodiments of the beam blocking material disclosed herein including a mixture of melted wax and fluorescent materials. The wax material preferably being the pattern wax material suitable for use in making turbine blade investment casting molds and the fluorescent preferably being material the fluorescent penetrant.

ADVANTAGES

The present invention has many advantages over beam drilling and inspection of airfoil and other cooling holes disclosed in the prior art. The present invention provides a more economical method and beam blocking material for forming and inspecting laser and other beam drilled cooling holes in turbine airfoils and other articles with cavities disclosed in the prior art. The beam blocking material and the inspection method of the present invention can be done with off the shelf commercial materials that are readily available in many shops where such methods are practiced. Furthermore, the inspection under the black light and the equipment used can easily be set up in such a shop. The hole detection of the present invention can be done visually by an operator using his eyes or by electronic equipment and computers that use more sophisticated techniques to determine hole size and other parameters that are disclosed in the prior art. The primary advantage of the present invention is the elimination of the need for a human operator to stick a pin into each hole or for a complicated laser device to be accurately aimed to illuminate the hole and another device to detect the hole as done in the prior art.

BRIEF DESCRIPTION OF THE DRAWINGS

The novel features believed characteristic of the present invention are set forth and differentiated in the claims. The invention, together with further objects and advantages thereof, is more particularly described in conjunction with the accompanying drawings in which:

DETAILED DESCRIPTION

Figure 1:
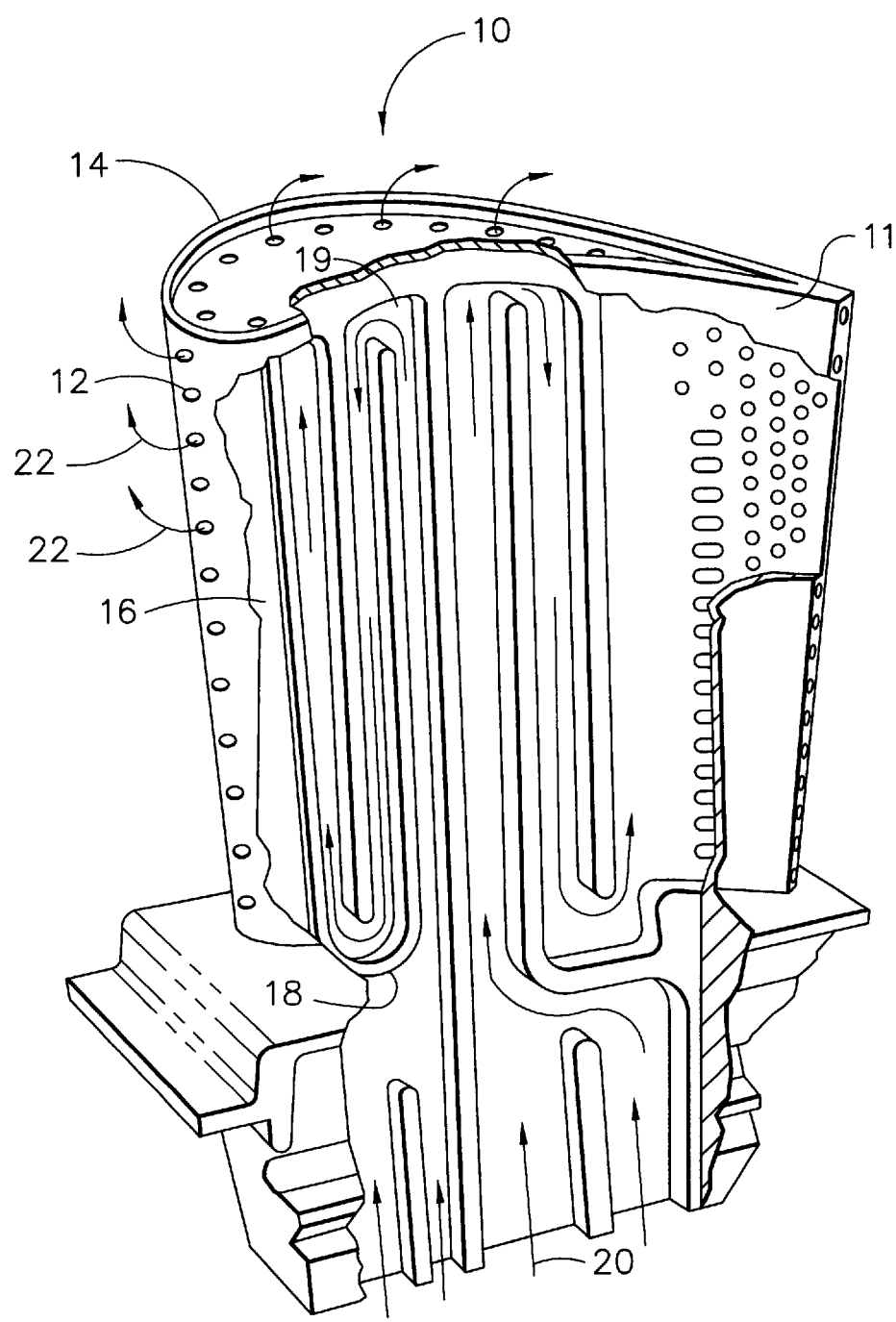
FIG. 1 is a partially cutaway perspective view of a turbine blade illustrating a conventional serpentine cooling path of the prior art.
Figure 2:
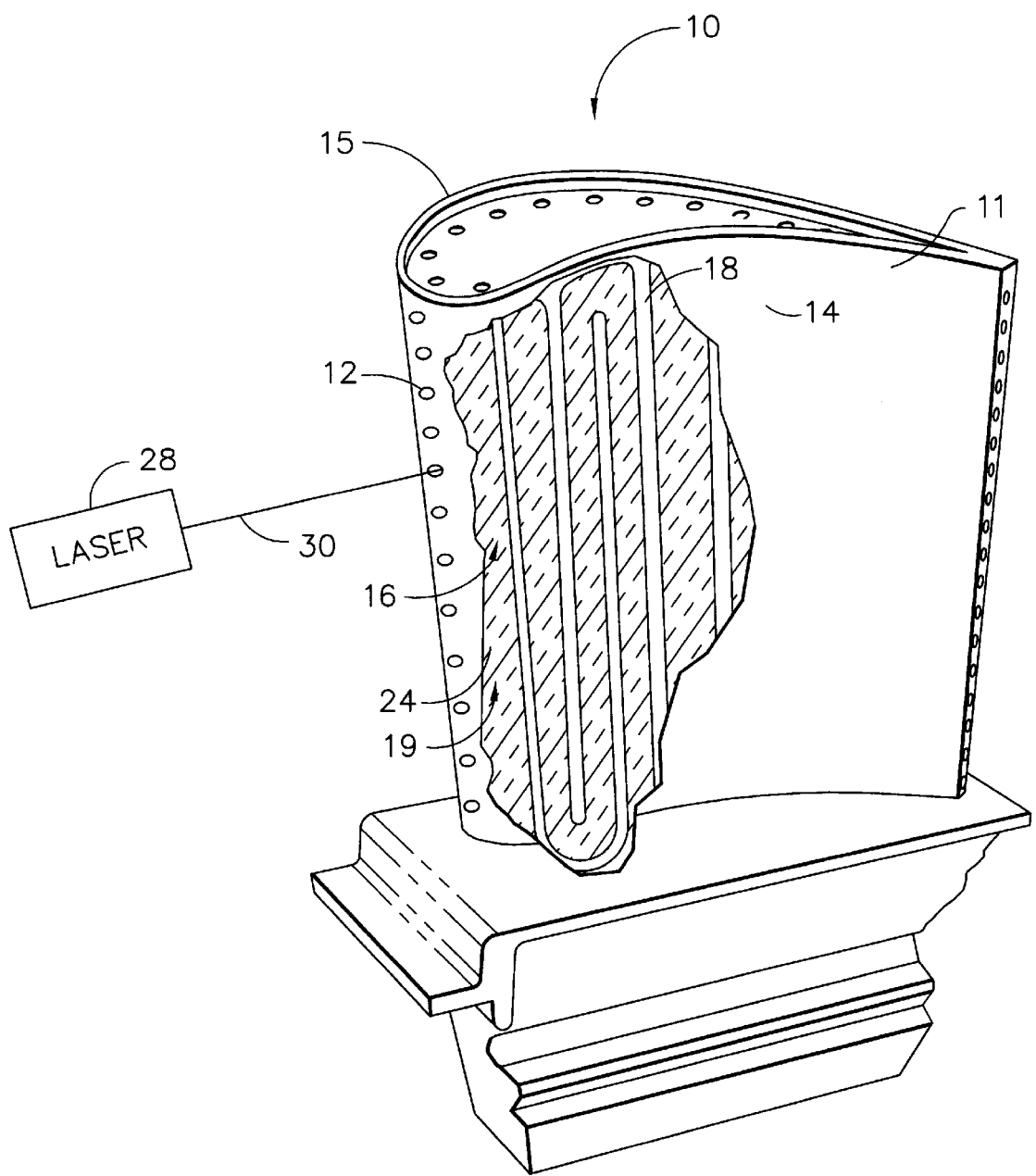
FIG. 2 is a perspective view illustrating laser cooling hole drilling of the turbine blade in FIG. 1 with a beam blocker material in accordance with the present invention.
Figure 3:
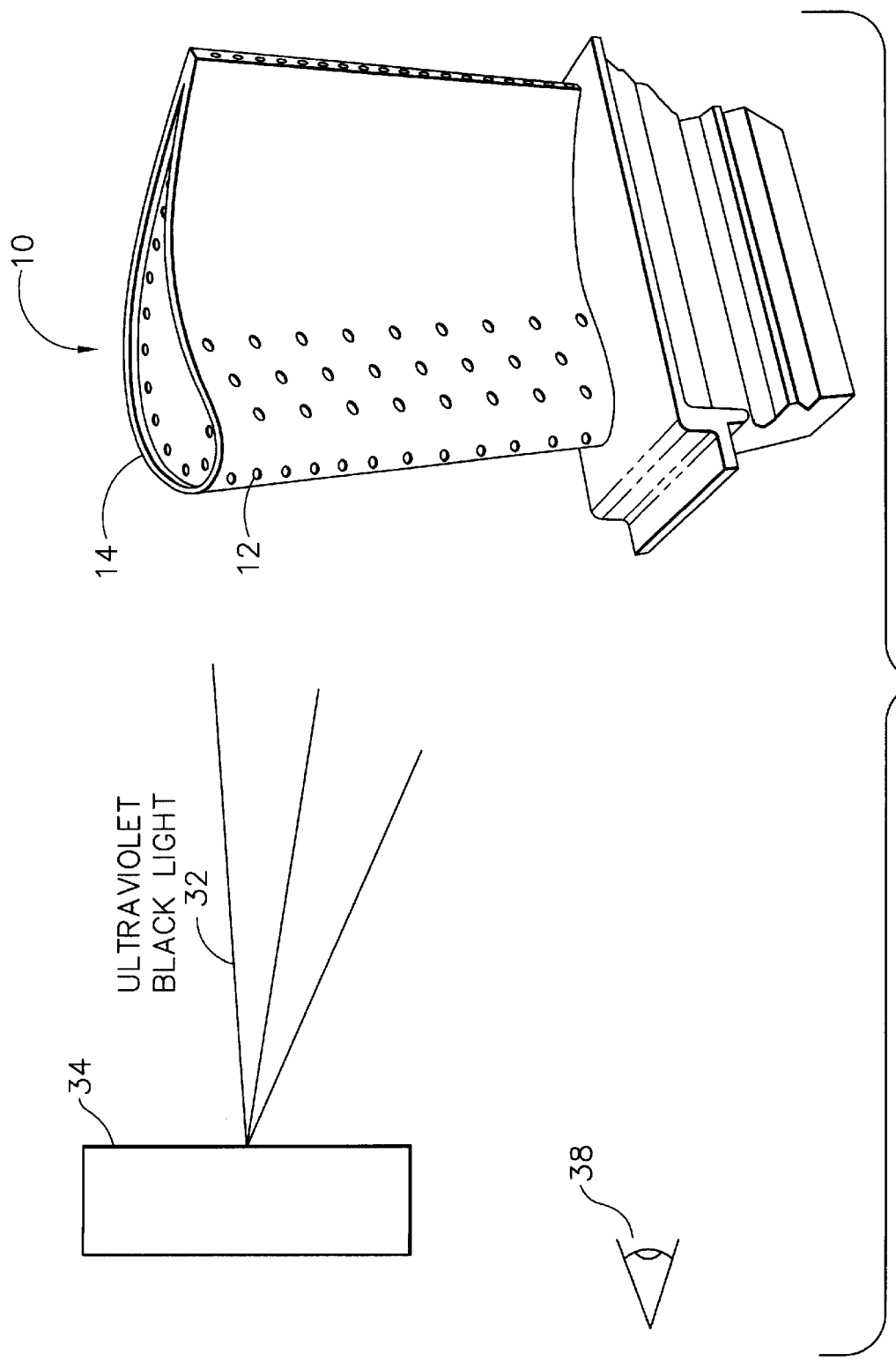
FIG. 3 is a perspective view illustrating laser cooling hole inspection of the turbine blade after the drilling illustrated in FIG. 1 in accordance with the present invention.
Figure 4:
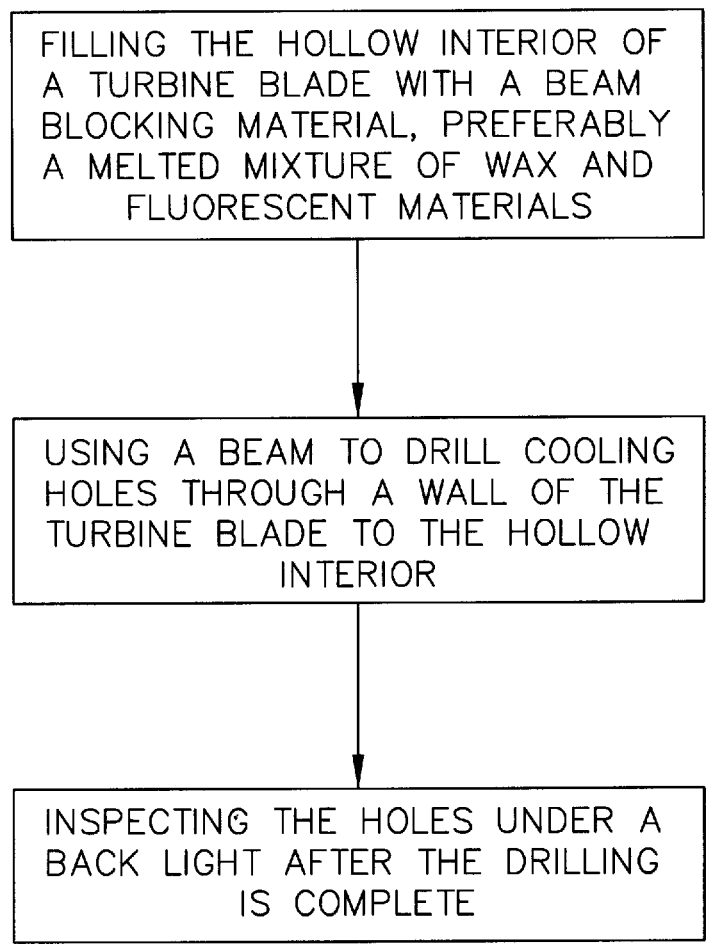
FIG. 4 is a flow chart illustrating a method of laser drilling cooling holes with a beam blocker material and inspection of the cooling holes in accordance with the present invention.

Referring now to the drawings, there is schematically illustrated in FIG. 1 a prior art example of a gas turbine engine blade 10 and airfoil 11 having a multiplicity of cooling channels or holes 12 formed therein by laser drilling to permit cooling of the blade during engine operation. The laser drilling method of the present invention is illustrated in FIG. 2 taken in conjunction with the flow chart illustrated in FIG. 4. The method of forming and inspecting beam drilled holes and, in particular, laser beam drilled holes 12 in an article such as a turbine vane or turbine blade airfoil 11, with a hollow interior 16 such as the serpentine cooling circuit 19. The method includes the following steps; (a) filling the hollow interior 16 (cooling circuit 19) with a beam blocking material 24 having fluorescent material, (b) preferably using a laser 28 and a laser beam 30 to drill the holes 12 in the wall 15 through to the hollow interior 16, and (c) inspecting the holes after the drilling is complete under an ultraviolet light 32 generated by a black light generator 34 as illustrated in FIG. 3. The hole detection and inspection in step (c) of the present invention can be done visually, by an operator using his eyes 38, or by electronic equipment and computers that use more sophisticated techniques to determine hole size and other parameters that are disclosed in the prior art.

The beam blocking material preferably includes a wax material and step (a) preferably includes filling the hollow interior with a melted mixture of the wax and fluorescent materials. The wax material may be a pattern wax material suitable for use in making turbine blade investment casting molds and the fluorescent material may be a fluorescent penetrant several of which are commonly known and used in the art to detect cracks. One such wax material that was tested is SW-12 Pattern Wax from Kindt-Collins Inc. of Dayton, Ohio which was mixed with a fluorescent penetrant named HM604 DUBL-CHEK Penetrant from Sherwin Inc. of Southgate, Calif. An airflow check may be used thereafter as is commonly done in the art to check for proper airflow through the serpentine cooling circuit and cooling holes.

The present invention also includes the various embodiments of the beam blocking material disclosed herein including a mixture of melted wax and fluorescent materials. The wax material preferably being the pattern wax material suitable for use in turbine blade investment casting mold making and the fluorescent preferably being material the fluorescent penetrant.

The foregoing descriptive embodiments of the invention have been presented for the purpose of describing and illustrating the invention. It is not intended to be exhaustive or to limit the invention to the precise form disclosed and obviously many modifications and variations are possible in light of the above teachings. While the preferred embodiment of the invention has been described fully in order to explain its principles, it is understood that various modifications or alterations may be made to the preferred embodiment without departing from the scope of the invention as set forth in the appended claims.

What is claimed is:

1. A method of forming and inspecting beam drilled holes in a wall of an article with a hollow interior, said method comprising:

(a) filling the hollow interior with a beam blocking material having fluorescent material, (b) beam drilling the holes in the wall through to the hollow interior, (c) illuminating a plurality of the holes simultaneously under an ultraviolet black light, and (d) inspecting the holes under the ultraviolet black light.

2. A method as claimed in claim 1 wherein said beam drilling step comprises laser drilling.

3. A method as claimed in claim 2 wherein said beam blocking material includes a wax material and step (a) includes filling the hollow interior with a melted mixture of the wax and fluorescent materials.

4. A method as claimed in claim 3 wherein said wax material is a pattern wax material suitable for use in making turbine blade investment casting molds.

5. A method as claimed in claim 4 wherein said fluorescent material is a fluorescent penetrant.

* * * * *